United States Patent [19]

Little

[11] Patent Number: 4,997,424

[45] Date of Patent: Mar. 5, 1991

[54] CATHETER INTRODUCER AND INTRODUCER SLITTER

[75] Inventor: Richard L. Little, Minneapolis, Minn.

[73] Assignee: MedAmicus, Inc., Minneapolis, Minn.

[21] Appl. No.: 333,253

[22] Filed: Apr. 5, 1989

[51] Int. Cl.$^5$ .......................................... A61M 25/00
[52] U.S. Cl. .................................. 604/280; 604/161; 30/90.4
[58] Field of Search ............... 604/160, 161, 164, 166, 604/280, 264; 30/90.1, 90.4, 90.8; 80/9.4, 9.51

[56] References Cited

U.S. PATENT DOCUMENTS

| | | | |
|---|---|---|---|
| 2,141,002 | 12/1938 | Huff | 81/9.5 |
| 3,902,501 | 9/1975 | Citron et al. | 128/418 |
| 4,394,828 | 7/1983 | Garbis | 30/90.8 |
| 4,451,256 | 5/1984 | Weitl | 604/164 |
| 4,631,059 | 12/1986 | Wolvek et al. | 604/280 |
| 4,687,469 | 8/1987 | Osypka | 604/161 |

Primary Examiner—Stephen C. Pellegrino
Attorney, Agent, or Firm—Clayton R. Johnson

[57] ABSTRACT

This invention relates to an introducer slitter for slitting an introducer tube portion having, for example, a catheter extending therethrough and into a body vessel while the introducer tube is moved rearwardly relative to the catheter to facilitate separating the introducer from the catheter without having to slide the introducer tube portion over the proximal end of the catheter. The slitter includes an arcuate section having an inner peripheral wall that extends arcuately through an angle of at least about 180° and is adapted to abut against the catheter, and a nose portion that extends between the catheter and introducer tube portions as the introducer is moved axially rearwardly relative to the catheter, a handle section extending radially outwardly of the arcuate section and a radially extending cutting edge for engaging the introducer tube portion for slitting the introducer tube portion as the introducer is pulled rearwardly relative to the slitter.

30 Claims, 2 Drawing Sheets

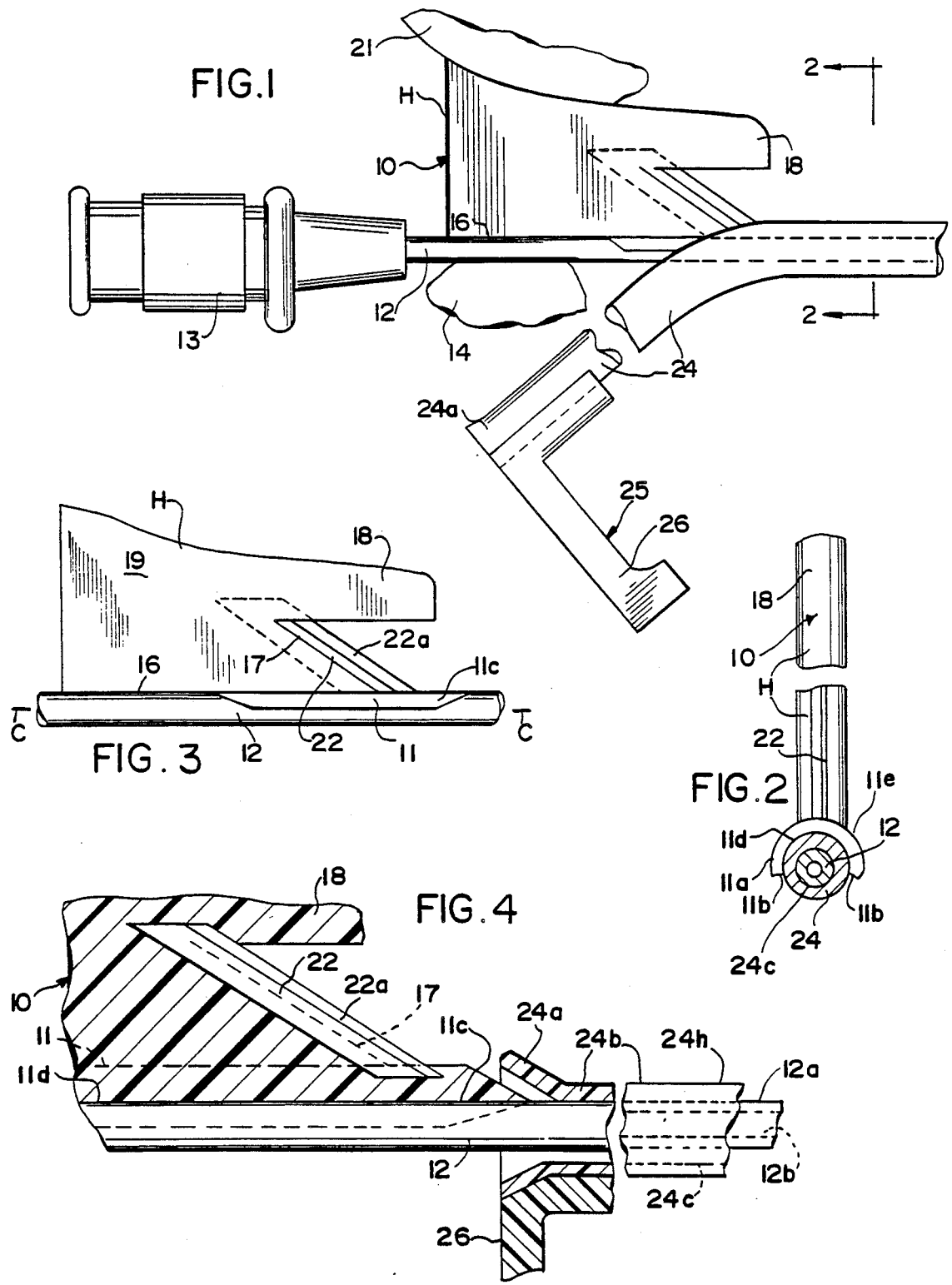

CATHETER INTRODUCER AND INTRODUCER SLITTER

BACKGROUND OF THE INVENTION

This invention relates to the removal of an introducer or cannula from a catheter, pacing lead, or similar item without having to pull the introducer over the proximal end of the catheter, and more particularly to a slitter device.

In my U.S. Pat. No. 4,214,594 there is disclosed a temporary lead assembly having a head portion for storing a cannula after the cannula has been used for extending the electrode end portion of the assembly into a body vessel.

U.S. Pat. No. 4,306,652 to Osborne discloses a flexible cannula that is made of a material having a molecular orientation whereby it will readily tear only in a longitudinal direction. As a result the cannula can be readily torn into two longitudinal sections for removal of the cannula from a catheter or similar device extending into a body vessel without having to slide over the proximal end of the catheter.

Another prior art cannula made to accomplish the same objects as that of the above Osborne patent is made of a different type material and has diametrically opposite score lines extending the length of the tubular part thereof to facilitate tearing the cannula into two axial half-sections.

A problem that at times is encountered with the cannulae referred to in the two preceeding paragraphs is that during tearing the cannula, one of the tabs together with the proximal part of the tube section joined thereto may break or otherwise separate from the more distal tubular part, or the cannula will not tear in a straight line and therefore not separate along the entire axial length of the tube section. As a result, it is necessary to use, for example a scalpel to cut the distal part of the cannula tubular portion. Using a scalpel may have adverse consequences, for example, cutting ones hand or the catheter.

SUMMARY OF THE INVENTION

An introducer slitter for longitudinally slitting a cannula or introducer to facilitate the removal of an introducer from a catheter extended therethrough. The slitter includes an arcuate section abuttable against the outer peripheral wall of a catheter, a handle section that extends away from the arcuate section opposite the catheter and a front cutting edge extending away from the arcuate section in the same direction as the handle section. The arcuate section has a nose portion to extend between the catheter and the introducer through which the catheter extends whereby as the introducer is pulled rearwardly relative to the cutting edge, the introducer tube is slit along its entire length so that the introducer can be removed from the catheter without withdrawing the catheter from the blood vessel and sliding the introducer over the proximal terminal end of the catheter. Additionally, this invention allows the physical removal of the introducer by using only two hands whereas the prior art requires two hands to tear the introducer and another hand to hold the catheter or pacing lead so that the catheter will not dislodge from its placement inside of a body vessel.

BRIEF DESCRIPTION OF THE DRAWINGS

FIG. 1 is a side view showing the first embodiment of the introducer slitter of the invention axially cutting the introducer to separate the introducer from a catheter;

FIG. 2 is a transverse cross sectional view that is generally taken along the line and in the direction of the arrows and along the lines 2—2 of FIG. 1;

FIG. 3 is an enlarged side view of the slitter of FIG. 1 positioned on a catheter;

FIG. 4 is an enlarged fragmentary longitudinal cross sectional view of part of the structure shown in FIG. 1 other than the introducer has not been pulled rearwardly a sufficient distance to start the slitting of the introducer and the differences of diameters of the inner peripheral wall of the introducer and the outer wall of the catheter being exaggerated;

Referring to FIGS. 1–4, the first embodiment of the slitter of this invention, generally designated 10, has an axially elongated, downwardly opening arcuate section 11 that is generally C-shape in transverse cross section. The downwardly extending legs 11a of the arcuate section are of sufficient resiliency that a tubular axial Portion 12 of a catheter which extends distally of the connector portion (fitting) 13 of the catheter may be pressed radially to abut against the inner peripheral wall 11d of the arcuate section even though the outer radius of curvature of the tubular portion 12 is not significantly less than the radius of curvature of the inner peripheral wall of the arcuate section. The connector may be any one of a number of conventional connectors used with, or forming the proximal end portion of the catheter. The catheter has inner and outer peripheral walls 12b, 12a. Even though the arcuate section can extend arcuately through 360° with a slit extending the axial length thereof, provided the legs are of sufficient resiliency, preferably the arcuate section extends through an angle greater than 180°, but advantageously less than 240°.

Figure 6:
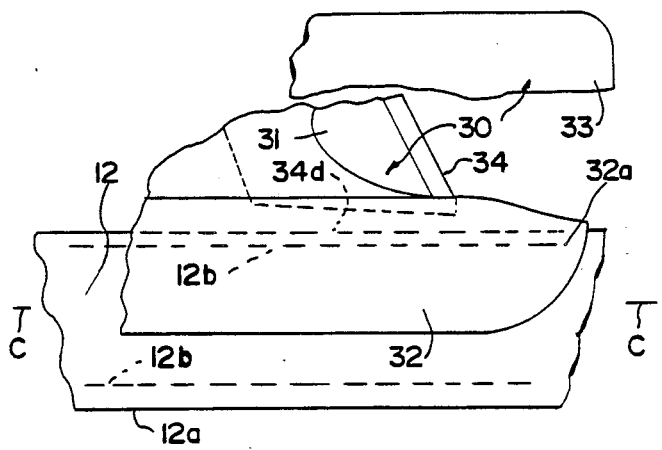
FIGS. 6 and 7 are fragmentary side views of the second and third embodiments of the introducer slitter of the invention.

The slitter 10 also includes an axially elongated handle section H that has its lower edge portion 16 integrally joined to the arcuate portion to extend thereabove and a front edge portion 17 that intersects with the lower edge portion 16 rearwardly of the front nose portion 11c of the arcuate section. Preferably the handle section H is transversely centered (transversely symmetrically) relative to the arcuate section and extends a significant distance rearwardly of the rear edge portion of the arcuate section, advantageously about the thickness of the average user's forefinger 14.

The handle section also has an upper front portion 18 that extends above the edge portion 17, forwardly of the rearwardmost part of the edge portion 17 and desirably forwardly of the nose section 11c. The top edge of the upper front portion and the upper rear portion 19 of the handle section is advantageously curved to facilitate having the ball of the thumb 21 of the user abutting thereagainst during use.

The handle section has the rear and top edge portions of a knife blade 22 embedded therein with the knife cutting edge 22a extending vertically (radially) between the upper front portion and the arcuate section ad forwardly of the edge portion 17. The knife blade lower edge portion is embedded in the arcuate section with the lower terminal edge radially between the inner and outer peripheral walls of the arcuate section and with the knife blade extending through the arcuate section outer peripheral wall 11e rearwardly of the nose portion. The apex 22c of the cutting edge portion 22a extends entirely within a radial plane that contains the central axis c—c of the arcuate section and is transversely centered relative to the arcuate legs 11a and the handle section. Preferably the handle section is substantially transversely symmetrical relative to the radial plane and preferably the entire cutting edge is located in said plane.

Desirably the radial outer surface of the nose portion diverges away from the central axis c—c of the inner peripheral wall 12d in a rearward direction to facilitated the entry of the arcuate section radially between the inner peripheral surface 24c of the tube portion 24 of the introducer, generally designed 25, and the outer peripheral surface 12a of the catheter as the introducer is moved rearwardly relative to the slitter and the catheter. The proximal portion 24a of the tube portion 24, at least that part radially remote from the tab portion 26, diverges away from the tube portion central axis in a rearward direction to facilitate the entry of the nose portion 11c as referred to above. The part 24a which advantageously is generally frustoconical is integrally joined to the proximal end of the generally constant diameter cylindrical tubular part 24b of the introducer tubular part 24, part 24b having inner and outer peripheral walls 24c, 24h respectively. The tab portion 26 of the introducer extends radially away from the tube portion 24 and facilitates pulling the introducer rearwardly with the hand of the user other than the one that has finger 14 and thumb 21.

The radial spacing of the lower edge of the entire upper portion 18 forwardly of the knife cutting edge from the arcuate section outer peripheral wall 11e is many times greater than the radial thickness of the introducer tube portion to be slit. Further the radial spacing of the upper portion 18 from the arcuate section and the distance that the arcuate section nose and upper portions extend axially forwardly of the cutting edge is desirably such that an average user can not move a finger relative to the cutting edge to cut the user's finger.

After the catheter or pacing lead has been extended through the introducer into the blood vessel, with the axially adjacent parts of the connector and the proximal terminal end of the introducer tube portion axially spaced by a dimension greater than the axial dimension from the distal end of the arcuate section to the proximal end of the lower terminal edge of the arcuate section, or the handle section, whichever extends the furtherest distance rearwardly, the catheter is pushed through the downwardly opening of the arcuate section with the nose portion extending toward the distal end of the catheter.

Due to the resiliency of the legs 11a, the relative radii of the inner peripheral wall 11d of the arcuate section and the outer peripheral wall 12a of the catheter and the axial length of the legs of the arcuate section, the slitting of the introducer tube is facilitated. Now with the slitter being held by one hand with the ball of the thumb pushing downwardly with the ball of the thumb pointing axially forwardly, and the crook of the forefinger forcing the adjacent part of the catheter against the rear, lower terminal edge of the handle section (part that extends rearwardly of the arcuate section) and the tab portion 26 extending downwardly relative to the handle section, the tab portion 26 is pulled rearwardly by the other hand. As a result the introducer is pulled rearwardly such that the rear part of the tube portion 24 is pulled over the nose portion, i.e. the nose portion enters radially between the catheter outer peripheral wall and the introducer tube portion inner peripheral wall. Then the proximal terminal edge of the introducer tube portion in being moved rearwardly abuts against the cutting edge to slit the tubular portion 24 and the slitted part is moved downwardly and rearwardly of the knife edge and the radially adjacent part of the catheter. Since the knife cutting edge portion diverges in a rearward direction and the axially adjacent parts of the front edge portion 17 desirably diverges in a rearward direction the slit edges of the introducer tube are transversely spread and thence further spread due to moving downwardly in a rearward direction over the arcuate section outer peripheral wall. Thus the introducer is removed from the catheter without having to be pulled over the connector proximal terminal end.

The introducer slitter may also be used for slitting an introducer on an electrode head assembly, for example of the type disclosed in my above mentioned patent.

FIG. 6 shows a second embodiment of the invention, generally designated 30, that is the same as the first embodiment other than the front edge 31 of the handle section is arcuately curved to extend upwardly and rearwardly of the nose portion 32a of the arcuate section 32 and thence curved (not shown) to extend upwardly and forwardly to intersect with the lower edge (not shown) of the upper portion 33 of the handle section. The handle section mounts the knife blade 34 in a manner similar to that described with reference to the first embodiment and as more clearly shown, with the knife blade lower edge radially between the arcuate section peripheral walls. The arcuate section has inner peripheral wall 34d to abut against the catheter 12.

Figure 7:
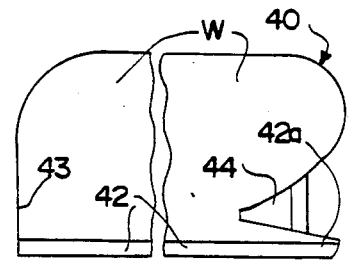

Referring to FIG. 7, the third embodiment, generally designated 40, is similar to that described with reference to the first embodiment other than for the shape of the handle section, that the arcuate section 42 extends rearward to adjacent to the rear terminal edge 43 of the handle section W, and the knife blade 44 has its cutting edge extending vertically. Thus even though it is desirable that the cutting edge extends radially away from the arcuate section in a rearward and upperward direction such as shown in FIGS. 4 and 6 it may be vertical (perpendicular to the central axis) such as shown in FIG. 7.

Figure 5:
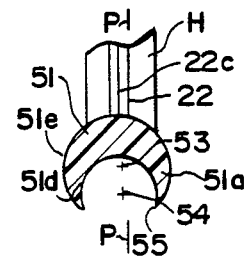
FIG. 5 shows the preferred shape of an arcuate section and the adjacent part of the handle section of this invention as seen in transverse cross section.

Even though the arcuate section may be shaped such as shown in FIG. 2 wherein the outer and inner peripheral walls 11c, 11d are arcuately curved about the central axis c—c and the legs have terminal edges 11b of widths about the same as the difference in the radii of curvature of the outer and inner peripheral walls, desireably the arcuate cross section in a transverse plane just forwardly of where the apex edge 22c of the knife intersects the outer peripheral wall is as shown in FIG. 5. That is each of the arcuate sections 11, 32 and 42 in the plane referred to in the preceeding paragraph may be such as shown in FIG. 5 where the arcuate section has outer and inner peripheral walls 51e, 51d.

The outer peripheral wall 51e is arcuately curved about an axis 53 located in plane P—P referred to with reference to FIG. 2. The inner peripheral wall 51d is arcuately curved about axis 54 which is the same as axis c—c of FIGS. 1, 6 and 7, and is located in plane P—P opposite axis 53 from the juncture of the handle section 11 to the arcuate section 51. The inner peripheral wall desireably extends arcuately through an angle of at least about 180°. The radius of curvature of the outer peripheral wall is greater than that of the radius of curvature of the inner peripheral wall and advantageously axis 53 is located radially between the inner Peripheral wall and axis 54. The inner and outer Peripheral walls intersect at the terminal edges 55 of the legs 51a of the arcuate section, the legs and edges (although not necessarily so) preferably being symmetrically located relative to the plane P—P.

Each of the embodiments may be used for more than one outer diameter catheter. However to cover the range of different diameter convention catheters, there would be provided slitters having arcuate sections with inner peripheral walls of different radii of curvature and legs of different arcuate dimensions so that they preferably will angularly encompass more than 180° of the catheter with which the particular slitter is being used. It is not essential that the arcuate section legs be resilient in that the catheter is resilient, but with the legs being resilient, the slitter can be used with more different diameter catheters. However if one of the catheter and legs is not resilient, the other should be resilient, the degree of resiliency depending upon the relative resiliency of one to the other.

Advantageously the arcuate and handle sections are formed as one integral unitary unit with the rear, top and bottom edge portions of the metal knife blade embedded therein. However both the knife and combination of the handle and arcuate sections may be formed as a single unitary unit, and may b made entirely of metal or plastic. The handle and arcuate sections are of sufficient rigidity to maintain their shapes (self sustaining) while the thickness of the handle section is greater than the radial thickness of the arcuate section throughout the angular and axial dimensions of the arcuate section. Further the legs are of sufficient resiliency that the catheter may be readily pushed upwardly between the axial terminal edges 11b (55) of the arcuate section 11a (51a) to abut against at least the top part of the inner peripheral wall of the arcuate section even though the arcuate section extends arcuately through an angle greater than 180°.

Additionally it is desirable that each leg extends the same distance arcuately away from the adjacent side of the part of the handle section joined to the arcuate section. Also the legs of the arcuate section desirably extend symmetrically away from the handle section, including to a plane that in turn is perpendicular to a plane tangential to the intersection (juncture) of the arcuate section to the handle section.

With the slitter a single slit is formed that extends the axial (longitudinal) length of the introducer tube and due to the resiliency of the introducer tub, the slitted edge portions may be moved radially away from the radial adjacent parts of the catheter tube. Thus the catheter relatively moves through the slit formed in the introducer tube portion as the introducer is moved rearwardly relative to the slitter and the catheter which is retained in a substantially fixed position relative to the radial adjacent parts of the slitter.

Although not preferred, the arcuate section inner peripheral wall may extend through 360° as long as it is axially slit its entire axial length at other than where the arcuate section is integrally joined to the handle section and the arcuate section is of sufficient flexibility (resiliency) that the slitter may be moved radially relative to the catheter to have the catheter enter radially between the slit edges and abut against the arcuate section inner peripheral wall.

Even though the slitter of this invention may be used with conventional introducers, desirably the slitter is used with the introducer 25. Even though the proximal terminal end portion 24a is shown as being frustoconical with a major base terminal edge and the minor base integrally joined to the constant inner and outer diameter, axially elongated tube part 24 that has a distal end not shown, only just the part of the proximal end portion opposite the tab portion may diverge from the central axis c—c in a a rearward direction. The tubular portion 24 may be of sufficient resiliency that when just the tab portion is vertical, the greater the distance that the tube portion extends away from the tab portion 26, the more it bends away from the horizontal (assuming the tubular portion is not precluded by some other object from doing so).

The tab portion advantageously is relatively rigid and of a substantially greater rigidity than the tubular portion. Further the tab portion extends radially away from the tubular portion a sufficient distance to be readily held by one finger and the thumb of one hand of the user. Thus the user can use one hand to hold the slitter and catheter in place and the other to pull the introducer rearwardly along the catheter to slit the introducer.

The tubular portion 24b has the outer and inner peripheral walls 24h, 24c with the inner peripheral wall being of a larger diameter than the outer diameter of the catheter and a central axis c—c. The showing of the relative inner and outer diameters of introducer portion 24 and the outer diameter of the catheter is exaggerated in FIG. 4. Advantageously the tab portion is made of the same material as the tubular portion 24 even though the tab portion may be of a higher density, for example both made of polyethylene. The tubular portion may be formed and then the the tab portion may be molded and at the same time be joined to the tubular portion. The introducer of this invention is provided with only one tab portion.

Even though not shown, the slitter of this invention, for example, that of FIG. 7, may have a second arcuate section joined to the top edge (edge opposite section 42) to open in a direction opposite the opening of the arcuate section 42. In such an event one of the arcuate sections has an inner peripheral wall of a radius of curvature for, as an example, a 7 French arcuate section and a 9 French arcuate section with the front top portion being shaped similar to the lower front section and the top terminal edge of the knife embedded in the top arcuate section. As a result by rotating the slitter of FIG. 7 180° about a horizontal axis, the modified slitter would have the arcuate section (not shown) function in the same manner as the arcuate section 42 other than with a different diameter catheter.

Figure 8:
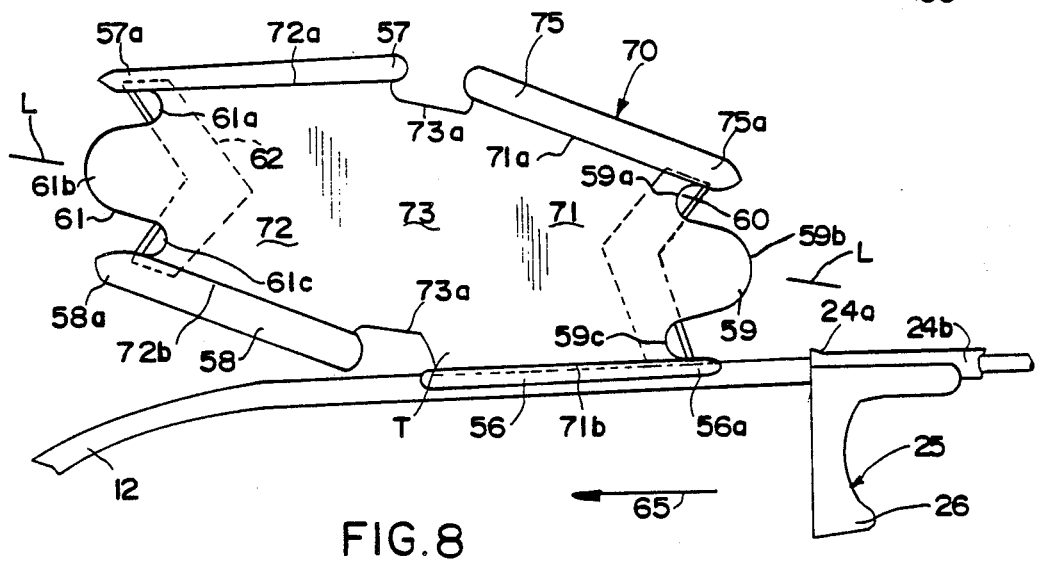
FIG. 8 is a side view of a fourth embodiment of the invention.

Referring to FIG. 8, the fourth embodiment of the invention, generally designated 70, includes a longitudinal axis L—L, and an elongated handle section T that has a first end portion 71, a second end portion 72 which is of the same shape and size as the first end portion except it is faced in an opposite direction, and an intermediate portion 73 extending between and at opposite ends is integrally joined to the first and second end portions respectively. The first end portion has transverse opposite, longitudinally extending edges 71a, 71b that are transversely spaced and diverge from one another and the axis L—L in a direction toward the second end portion. Likewise the second end portion has transversely spaced, opposite edge portions 72a, 72b that diverge from one another and the axis L—L in a direction toward the first end portion. Advantageously the angles of divergence are such that the respective pair of edges extend predominantly longitudinally.

Integrally joined to edges 71a, 71b, 72a, 72b are the elongated arcuate sections respectively. Advantageously each of the arcuate sections is of the same construction as arcuate sections 32, or 42, or 51, other than the inner peripheral walls of arcuate sections 75, 56–58 are of different radii of curvature. The arcuate sections each open outwardly from the respective edge to which it is joined with the arcuate sections inner peripheral walls central axes being parallel to the respective edge.

The first portion 71 has a transverse terminal edge 59 that extends between and intersects with the outer peripheral walls of the arcuate sections 75, 56 to have the nose portions 75a, 56a extend a short distance more remote from the second portion 72 than the respective intersection. A somewhat V-shaped knife 60 has one longitudinal edge embedded in arcuate section 75 and a transversely opposite edge embedded in arcuate section 56 with the knife cutting edge extending longitudinally more remote from the second portion 72 (exposed) than the reversely curved terminal edge portion 59a that intersects with arcuate section 75, and a reversely curved terminal edge portion 59c which intersects with arcuate section 56. The terminal edge 59 also has a transverse edge portion 59b extending between portions 59a, 59c and longitudinally more remote from the cutting edge portions of knife 60 than the second section 72. The transversely opposite edges of the knife are embedded in the arcuate sections to terminate between the respective arcuate section inner and outer peripheral walls such as indicated with reference to the FIG. 4 and 6 embodiments.

The second portion 72 has a generally transverse terminal edge 61 that is shaped the same as edge 59 except for being oppositely faced and has an edge portion 59a that intersects with arcuate section 57 more closely adjacent to the first portion 71 than the nose portion 57a of the arcuate section 57, edge portion 61c that intersects with arcuate section 58 more closely adjacent to the first portion 71 than the nose portion 58a of arcuate section 58 and an intermediate edge portion 61b. The second portion 72 mounts a knife blade 62 to have its cutting edge extend longitudinally more remote from handle portion 71 than the terminal edge portions 61a, 61c, but less remote than edge portion 61b, and transversely opposite edges embedded in arcuate section 57, 58 in a manner similar to that described with reference to knife 60. The terminal edges 59, 61 are shaped to in conjunction with the arcuate sections, preclude the users cutting their fingers as previously referred to with reference to other embodiments. Even though knifes 60, 62 are referred to as two knifes, it is to be understood that there may be provided a knife for each of edge portions 59a, 59b, 61a, 61c for longitudinally slitting an introducer tubular portion in a manner described with reference to other embodiments, depending upon which arcuate section has its inner peripheral wall abutting against a catheter.

The intermediate portion 73 has transversely opposite longitudinal terminal edges 73c that are more closely adjacent to the axis L—L than the longitudinally adjacent, transverse remote edge portions of the legs of arcuate sections 75, 56—58 from axis L—L. The intermediate portion 73 serves to longitudinally separate the adjacent parts of arcuate sections 75, 57 and 56, 58 respectively, and the angles of divergence from the longitudinal axis L—L facilitate using the desired one of the arcuate sections with a catheter radially between the arcuate section legs and slitting an introducer tubular portion without interference by the other arcuate section on the same transverse side of axis L—L.

The arcuate section 75, 56, 57, 58 may have inner peripheral walls of radii of curvature for, as an example, a 10, 7, 9, and 11 French size catheter respectively., and in transverse cross section be shaped such as shown in FIG. 5. For example if the catheter is of a size that arcuate section 57 is to be used the fourth embodiment is rotated 180° about each of the longitudinal and transverse axes from that shown in FIG. 8 and the catheter is pressed into the arcuate section 57 with its nose portion extending so as to enter between the tubular portion 24 and catheter 12 as the tab portion 26 is pulled rearwardly (arrow 65) relative to the catheter. Thus the fourth embodiment can be used for slitting introducers with a plurality of different size catheters, and more different sizes than with the other embodiments that have been described prior to the fourth embodiment. Of course it is to be understood that, depending upon the shape and size of the handle section any desired reasonable number of arcuate sections of different French sizes may be joined thereto.

In using the fourth embodiment of the invention, it can be held between the forefinger and the thumb of one hand abutting against opposite sides of the handle section, and if necessary, depending upon the resiliency of the arcuate section legs and the transverse dimensions and curvature of the legs inner peripheral walls, the same forefinger can be bent so as to hold the catheter within the arcuate section in abutting relationship to the arcuate section inner peripheral wall. The comments previously made relative to the relative resiliency of the arcuate section legs and the catheter are applicable to the fourth embodiment.

Even though not shown, the handle section of any one of the first three embodiments may have a top portion joined to the top edge of the respective handle section shown that extends transversely on either side of the sides of the handle section shown, and of an appropriate length.

With the slitter of this invention, the introducer tubular portion does not have to be made of a material such as disclosed in U.S. Pat. No. 4,306,652 or diametrically opposite score lines.

What is claimed is:

1. An introducer slitter for facilitating the removal of an introducer from a catheter or pacer lead that extends through the introducer and has its distal end extended into a body vessel without sliding the introducer tubular portion over the proximal end of the catheter wherein the catheter has a distal end and the catheter and introducer each have an axially elongated tubular portion with inner peripheral and outer peripheral walls, comprising an axially elongated handle section having a rear edge, a lower edge portion and a front edge portion, means defining a cutting edge joined to the handle section to extend forwardly of the axially adjacent part of the front edge portion and an axially elongated arcuate section joined to the lower edge portion to extend therebeneath and is transversely curved to open downwardly, the cutting edge having an axially adjacent part radially adjacent to the arcuate section, the arcuate section having a front nose portion extending axially forwardly of the axially adjacent part of the cutting edge for entering between the introducer inner wall and the catheter outer peripheral wall as the introducer is pulled rearwardly relative to the catheter tubular portion whereby the cutting edge axially slits the introducer tubular portion.

2. The slitter of claim 1 further characterized in that the arcuate section has axially elongated, arcuately opposite lower terminal edges that are substantially symmetrically located relative to the juncture of the arcuate section to the handle section.

3. The slitter of claim 1 further characterized in that the arcuate section has an inner peripheral wall that extends arcuately through an angle of at least about 180° and less than about 240°.

4. The slitter of claim 1 further characterized in that the arcuate section terminates sufficiently axially forwardly of the rear edge to permit a user's forefinger to hold the radial adjacent part of the catheter against the lower edge portion without having the finger abut against the arcuate section.

5. The slitter of claim 1 wherein the catheter has a catheter section, further characterized in that the arcuate section has an inner peripheral wall and that the arcuate section has transversely opposite arcuate resilient legs defining part of the arcuate section inner peripheral wall, and that the radii of curvature of the inner peripheral wall and the catheter together with the resiliency of the legs relative to that of the catheter preclude the catheter section that extends within the arcuate section radially adjacent to the arcuate section inner peripheral wall easily sliding with the arcuate section and accordingly not require any finger pressure to hold the catheter substantially fixed relative to the slitter as the introducer tubular portion is slit.

6. The slitter of claim 1 further characterized in that the arcuate section has transversely opposite terminal edges that extend the axial length thereof and an inner peripheral wall that extends arcuately through an angle of at least about 180°.

7. The slitter of claim 1 further characterized in that said means comprises a knife blade having the cutting edge.

8. The slitter of claim 7 further characterized in that the knife blade has a rear portion embedded in the handle section and a lower end portion embedded in the arcuate section.

9. The slitter of claim 8 further characterized in that the arcuate section has an inner peripheral wall, that the knife lower edge portion terminates radially outwardly of the arcuate section inner peripheral wall and that the handle section has an upper front portion that extends axially forwardly of at least part of the cutting edge and is radially spaced from the arcuate section.

10. The slitter of claim 1 further characterized in that said arcuate section has an inner peripheral wall adapted to abut against the catheter outer peripheral wall and extends arcuately through at least about 180° and that the handle section has a top portion radially spaced from the arcuate section and extends axially forwardly of at least part of the cutting edge.

11. The slitter of claim 10 further characterized in that the arcuate section has an outer peripheral wall, that the front nose portion in part defines the arcuate section inner and outer peripheral walls, and that the cutting edge extends radially between the arcuate section outer peripheral wall and the top portion, the cutting edge at the arcuate section outer peripheral wall being rearwardly of the nose portion.

12. The slitter of claim 11 further characterized in that the arcuate section has a central axis and that the nose portion outer peripheral wall portion in a rearward direction diverge from the central axis.

13. The slitter of claim 10 characterized in that the introducer tubular portion has a proximal end portion and only one tab portion joined to the introducer proximal end portion to extend radially therefrom to facilitate pulling the introducer tubular portion rearwardly along the catheter in a direction axially away from the catheter distal end, the introducer tubular portion has a central axis and the introducer proximal end portion has at least an arcuate part radially opposite the tab portion that diverges from the central axis in a rearward direction to facilitate the entry of the nose portion between the introducer tubular portion and the catheter as the introducer tubular portion is pulled rearwardly along the catheter to engage the cutting edge.

14. The slitter of claim 12 further characterized in that the front portion extends further forwardly than the entire cutting edge and that said means comprises a knife blade having said cutting edge and a lower terminal edge radially between the arcuate section inner peripheral wall and the top portion.

15. The slitter of claim 12 further characterized in that the handle and arcuate sections are substantially symmetrical relative to a plane containing the central axis and that the cutting edge is located within said plane for at least substantially its length between the arcuate section and top portion.

16. The slitter of claim 1 wherein the catheter has a proximal end, further characterized in that the arcuate section has an inner peripheral wall and that the arcuate section has transversely opposite, arcuately curved legs means defining part of the arcuate section inner peripheral wall for encompassing a part of a catheter and holding the catheter in a substantially fixed condition relative to the slitter handle section to slit the introducer tubular portion as the introducer is pulled along the catheter in a direction away from the catheter distal end, the leg means having transverse opposite arcuately curved resilient legs, the arcuate section having transversely opposite terminal edges extending the axial length thereof and constituting transverse terminal edges of the leg means that are sufficiently transversely spaced to permit a user having one hand holding the slitter with a finger of the same hand abutting against the catheter as the introducer is being slit, the leg means terminal edges being of a spacing and the leg means being of a resiliency for allowing the handle section being moved radially toward the catheter central axis to permit entry of the catheter being moved transversely between the leg means transverse edges and into engagement with the arcuate section inner peripheral wall, the arcuate section inner peripheral wall extending arcuately through an angle of at least 180 degrees and less than about 240 degrees, that the means having the cutting edge comprises a knife blade having the cutting edge and a lower edge portion embedded in the arcuate section and an upper unembedded portion and that the nose means extends axially forwardly of the leg means and the unembedded portion for entering radially between the introducer and catheter wall portions as the introducer is pulled in a direction away from the said user's hand, catheter and slitter.

17. A slitter according to claim 1, characterized in that the handle section has a top portion that at least in part extends forwardly of the cutting edge and radially spaced therefrom, that the handle and arcuate sections are substantially symmetrical relative to a plane containing the central axis and that the cutting edge is located within said plane for at least substantially its axial length between the arcuate section and the handle section top portion.

18. A slitter according to claim 1, characterized in that the arcuate section terminates sufficiently forwardly of the handle section rear edge to permit a user's finger engaging the catheter beneath the handle section without engaging the arcuate section and that the cutting means includes a knife section having a lower edge portion embedded in the arcuate section radially between the arcuate section inner and outer peripheral walls, the cutting edge extending above the arcuate section.

19. An introducer slitter to axially slit an introducer on a catheter that extends though the introducer and has its distal end extended into a body vessel for facilitating the removal of an introducer from the catheter without sliding the introducer tubular portion over the proximal end of the catheter wherein the catheter and introducer have axially elongated tubular portions with inner peripheral and outer peripheral walls, comprising an axially elongated handle section having a rear edge, a lower edge portion and a front edge portion, means defining a cutting edge joined to the handle section to extend forwardly of the axially adjacent part of the front edge portion and an axially elongated arcuate section that is joined to the lower edge portion to extend therebeneath and is transversely curved through an angle of at least about 180° to open downwardly for having the catheter extend into the arcuate section to abut against the inner peripheral wall of the arcuate section and have the cutting edge engage the introducer as the introducer is pulled rearwardly along the catheter relative to the cutting edge and catheter, the arcuate section having an outer peripheral wall and an inner peripheral wall for at least partially encompassing the catheter and the cutting edge extending above the arcuate section, including the arcuate section outer peripheral wall.

20. The slitter of claim 19 further characterized in that the arcuate section has a front nose portion that extends forwardly of the cutting edge and that the handle section has an upper front edge portion that at least i part extends forwardly of the cutting edge and has a lower front edge that is radially spaced from the arcuate section by a distance many times greater than the thickness of the introducer tube portion and extends forwardly of at least part of the cutting edge.

21. An introducer that is adapted to be slit along its entire axial length while having a catheter extended therethrough by a slitter that has an arcuate section front nose portion while the catheter extends within a body vessel, comprising an axially elongated tubular portion having a central axis and a proximal end portion, a tab portion joined to the proximal end portion to extend radially therefrom and being adapted to be grasped by the user to pull the tubular portion rearwardly along the catheter, the proximal end portion having an arcuate part arcuately offset from the juncture of the handle to the proximal end portion that diverges away from the central axis in a rearward direction to facilitate the entry of the nose portion radially between the catheter and tubular portion.

22. The apparatus of claim 18, further characterized in that only one tab portion is joined to the tubular portion.

23. The apparatus of claim 19 wherein the tubular portion is of a relatively thin wall construction to make it flexible and that the tab portion is of a thicker wall construction to make it relatively rigid.

24. The apparatus of claim 19 wherein the tubular portion has inner and outer peripheral walls and the arcuate section has an inner peripheral wall adapted to abut against the catheter outer peripheral wall, the tubular portion inner peripheral wall is of a larger diameter than the catheter outer peripheral wall and the tubular portion proximal end portion is frustoconical.

25. An introducer slitter for facilitating the removal of an introducer from a catheter or pacer lead that extends through the introducer and has its distal end extended into a body vessel without sliding the introducer over the proximal end of the catheter wherein the catheter and introducer each have an axially elongated tubular portion with inner and outer peripheral walls, comprising a longitudinally elongated handle section having a longitudinal axis, a first edge transversely spaced from the longitudinal axis, a terminal second edge intersecting and extending transversely away from the first edge, a longitudinally elongated arcuate section joined to the first edge, having an inner peripheral wall that has a central axis and is adaPted to abut against the catheter outer peripheral wall, a slit extending the longitudinal length thereof to form two arcuate section longitudinal terminal edges to permit the catheter being moved radially therebetween for abutting against the arcuate section inner peripheral wall and a nose section adapted to enter between the introducer tubular portion and the catheter as the introducer is pulled toward the second edge, and a knife portion mounted at least in part by the handle section and having an exposed cutting edge longitudinally adjacent to the second edge to axially slit the introducer tubular portion after the nose portion enters between the introducer tubular portion and the catheter.

26. The slitter of claim 22 further characterized in that the arcuate section inner peripheral wall extends transversely through an arcuate angle of at least about 180°.

27. The slitter of claim 23 further characterized in that the handle section has a third edge that is transversely opposite of the longitudinal axis from the first edge and a terminal fourth edge that extends transversely relative to the third edge and intersects the third edge, a longitudinally elongated second arcuate section having an inner peripheral wall that has a central axis and of a different radius of curvature than the first arcuate section inner peripheral wall and a nose portion adapted to enter between a catheter and an introducer tubular portion as the introducer is moved along the catheter toward the fourth edge and an exposed knife blade second portion extending longitudinally away from the fourth edge to slit the introducer tubular portion after the second arcuate section nose portion enters between the tubular portion and the catheter.

28. The slitter of claim 24 further characterized in that the arcuate sections along their lengths in a direction away from their nose portions diverge from one another and the longitudinal axis.

29. The slitter of claim 25 further characterized in that the handle section has a longitudinal first portion having the handle section first through fourth edges, a longitudinal second portion and an intermediate portion extending longitudinally between the first and second handle portions, the second handle portion having a longitudinal fifth edge on the same transverse side of the longitudinal axis as the first edge and a transversely extending terminal sixth edge that intersects with the fifth edge and a longitudinally elongated third arcuate section joined to the fifth edge and having a terminal nose portion longitudinally remote from the first arcuate section, and an inner peripheral wall having terminal edges extending the length thereof to have a catheter moved radially therebetween, and being of a radius of curvature different from the radii of curvature of the inner peripheral wall of the first and second arcuate sections, and a knife portion having an exposed cutting edge extending transversely away from the sixth terminal edge for slitting an introducer tubular portion after the third arcuate section nose portion enters between the catheter and introducer tubular portion as the introducer tubular portion is moved along the catheter toward the first handle portion, the fifth edge diverging from the longitudinal axis in a direction toward the handle section first portion.

30. An introducer in combination with an introducer slitter for removing the introducer from a catheter or pacer lead that has an axially elongated tubular portion having a central axis, inner and outer peripheral walls, extends through the introducer and has its distal and extended into a body vessel without having to slid the introducer off the catheter tubular portion, the introducer having an axially elongated tubular portion that has inner and outer peripheral walls and a proximal end portion and only one tab portion joined to the introducer proximal end portion to extend radially therefrom to facilitate pulling the introducer tubular portion rearwardly along the catheter, the introducer tubular portion having a central axis and the introducer proximal end portion having at least an arcuate part radially opposite the tab portion that diverges from the central axis in a rearward direction to facilitate the entry of the slitter between the introducer tubular portion and the catheter as the introducer tubular portion is pulled rearwardly along the catheter to slit the introducer tubular portion radially opposite from the direction that the tab extends therefrom as the tab portion is pulled in a direction away from the catheter distal terminal end, and the slitter having an axially elongated handle section that has a rear edge, a lower edge portion and a front edge portion, a knife blade having a cutting edge mounted by the handle section to extend forwardly of the axially adjacent part of the front edge portion and an axially elongated arcuate section that is joined to the lower edge portion to extend therebeneath and is transversely curved to open downwardly, the arcuate section having a front nose port extending axially forwardly of the axially adjacent part of the cutting edge to enter into between introducer arcuate part and the catheter outer peripheral wall portion as the introducer is pulled axially away from the catheter distal end portion whereby the cutting edge axially slits the introducer tubular portion, the arcuate section having a peripheral wall portion that is transversely curved through an angle of at least about 180 degrees to open downwardly for having the catheter extended into by moving the handle section radially toward the catheter central axis.

* * * * *